United States Patent
Ahn (10) Patent No.: US 11,382,668 B2
(45) Date of Patent: Jul. 12, 2022

(54) BONE FIXATION SCREW STRUCTURE

(71) Applicants: GBS Commonwealth Co., Ltd., Seoul (KR); PMT Republic, Inc., Walnut, CA (US)

(72) Inventor: Kyoung Gee Ahn, Seoul (KR)

(73) Assignees: GBS COMMONWEALTH CO., LTD., Seoul (KR); PMT REPUBLIC, INC., Walnut, CA (US)

( * ) Notice: Subject to any disclaimer, the term of this patent is extended or adjusted under 35 U.S.C. 154(b) by 0 days.

(21) Appl. No.: 17/411,642

(22) Filed: Aug. 25, 2021

(65) Prior Publication Data

US 2022/0061890 A1 Mar. 3, 2022

(30) Foreign Application Priority Data

Aug. 27, 2020 (KR) .......................... 10-2020-0108810

(51) Int. Cl.
*A61B 17/70* (2006.01)
(52) U.S. Cl.
CPC ...... *A61B 17/7032* (2013.01); *A61B 17/7082* (2013.01)
(58) Field of Classification Search
CPC .............. A61B 17/708; A61B 17/7077; A61B 17/7079; A61B 17/7082; A61B 17/7083; A61B 17/7085; A61B 17/7086; A61B 7/7088; A61B 7/7089

USPC .......................................................... 606/246
See application file for complete search history.

(56) References Cited

U.S. PATENT DOCUMENTS

| | | | | |
|---|---|---|---|---|
| 2015/0148849 A1* | 5/2015 | Abidin | ................. | A61B 17/708 606/279 |
| 2016/0008034 A1* | 1/2016 | Stokes | ............... | A61B 17/7085 606/278 |
| 2019/0343558 A1* | 11/2019 | Farmer | ............... | A61B 17/7082 |
| 2020/0170690 A1* | 6/2020 | Krause | ............... | A61B 17/7082 |

* cited by examiner

*Primary Examiner* — Eduardo C Robert
*Assistant Examiner* — Christina Negrellirodriguez
(74) *Attorney, Agent, or Firm* — Novick, Kim & Lee, PLLC; Jae Youn Kim (57) ABSTRACT

Disclosed is a bone fixation screw structure, particularly a bone fixation screw structure including a receiver configured to provide a space in which a bone screw is inserted into the lower end thereof, a pair of openings formed at facing sides of the receiver and provided in an open form along a longitudinal direction of the receiver, and a pair of closures formed at remaining facing sides of the receiver and provided in a closed form along the longitudinal direction of the receiver, thereby enabling a user to easily change a closed-type receiver to an open-type receiver and thus fundamentally preventing interference with a rod or an insert component.

6 Claims, 9 Drawing Sheets

BONE FIXATION SCREW STRUCTURE

BACKGROUND OF THE INVENTION

Field of the Invention

The present invention relates to a bone fixation screw structure, and more particularly to a bone fixation screw structure capable of being easily changed from a closed type to an open type according to a user's convenience and preventing interference with an insert component.

Description of the Related Art

The spine is a bone structure that forms the spinal column, connects the skull to the pelvis, and supports the body while forming the central axis thereof. It is composed of cervical vertebrae, thoracic vertebrae, lumbar vertebrae, sacral vertebrae, and coccygeal vertebrae.

The spine having such a structure and function is damaged or deformed due to an external shock caused by an accident or incorrect posture for a long period of time. Hence, a bone fixation screw is required to correct such a damaged or deformed spine.

In general, a bone fixation screw device is used to physically correct or fix the vertebrae in a state of being joined to each of adjacent vertebrae. Vertebral fixation using such a bone fixation screw device is performed in a manner in which bone screws are inserted into respective vertebrae and interconnected and fixed using a rod that is disposed almost parallel to the longitudinal direction of the spine.

The bone fixation screw device includes a receiver, configured to accommodate a bone screw to be inserted into a vertebra, and a rod. The bone screw may include a monoaxial screw incapable of moving with respect to the receiver or a polyaxial screw capable of freely moving with respect to the receiver.

Specifically, bone screws are screwed into vertebrae, and when the bone screws are correctly placed, a rod is installed in each receiver to connect the bone screws to each other. The rod is then secured by means of a fastening screw, plug or similar type of fastener.

Here, depending on the shape of the upper end, opposite which the bone screw is accommodated, the receiver may be classified into a closed type in which the upper end is closed and an open type in which the upper end is open.

Since the conventional closed-type receiver is configured such that the upper end thereof is closed, it is possible to prevent deformation such as distortion or the like of the receiver during the procedure, but there is a problem in that the upper end interferes with a rod or an insert component to which the rod is connected, making surgery difficult.

Moreover, in order to solve the problem with the closed-type receiver, when interference occurs, the connector of the upper end thereof may be cut using a tool, but the remainder of the connector of the upper end is still left behind in the vicinity of the cut site, so interference cannot be fundamentally prevented.

Furthermore, the conventional receiver is separately produced in two types, the closed type and the open type, and since the difference between the closed type and the open type lies in user preference, products of both types inevitably have to be manufactured, which is undesirable.

The matters described in the related art are only for improving understanding of the background of the present invention, and should not be taken as an acknowledgment that they correspond to conventional techniques already known to those of ordinary skill in the art.

SUMMARY OF THE INVENTION

The present invention has been made keeping in mind the problems encountered in the related art, and an objective of the present invention is to provide a bone fixation screw structure capable of fundamentally preventing interference with a rod or an insert component because a closed type may be easily changed to an open type by a user.

Another objective of the present invention is to provide a bone fixation screw structure capable of unifying production because there is no need to produce both the closed type and the open type according to the user preference.

The objectives of the present invention are not limited to the foregoing, and other objectives not mentioned herein will be clearly understood by those of ordinary skill in the art from the description of the present invention.

In order to accomplish the above objectives, the present invention provides a bone fixation screw structure including a receiver configured to provide a space in which a bone screw is seated at the lower end thereof, a pair of openings formed at facing sides of the receiver and provided in an open form along a longitudinal direction of the receiver, and a pair of closures formed at remaining facing sides of the receiver and provided in a closed form along the longitudinal direction of the receiver.

Also, in the bone fixation screw structure according to an embodiment of the present invention, at least one concave portion may be formed in the end of each of the pair of closures.

Also, in the bone fixation screw structure according to an embodiment of the present invention, the concave portion may be provided in a form that is recessed toward a center direction by cutting a portion of each of the pair of closures.

Also, in the bone fixation screw structure according to an embodiment of the present invention, a pair of concave portions may be formed to face each other in each of the pair of closures.

Also, in the bone fixation screw structure according to an embodiment of the present invention, the pair of concave portions facing each other may be connected to each other via a concave cutout.

Also, in the bone fixation screw structure according to an embodiment of the present invention, the width of the concave cutout may be smaller than the outermost diameter of the receiver.

Also, in the bone fixation screw structure according to an embodiment of the present invention, at least one concave notch may be formed in the outer surface or the inner surface of the concave cutout.

Also, in the bone fixation screw structure according to an embodiment of the present invention, ends of the pair of openings may be connected to each other by at least one connector.

Also, in the bone fixation screw structure according to an embodiment of the present invention, at least one connection notch may be formed in the upper surface or the lower surface of the connector.

Also, in the bone fixation screw structure according to an embodiment of the present invention, a plurality of through-holes may be spaced apart from each other in a longitudinal direction in each of the pair of closures.

BRIEF DESCRIPTION OF THE DRAWINGS

The above and other objectives, features and other advantages of the present invention will be more clearly understood from the following detailed description taken in conjunction with the accompanying drawings, in which.

DETAILED DESCRIPTION OF THE INVENTION

Hereinafter, a detailed description will be given of the present invention in conjunction with the accompanying drawings so that those of ordinary skill in the art can easily implement the present invention. However, the present invention may be embodied in a variety of different forms and is not limited to the embodiments described herein.

In order to clearly explain the present invention, parts irrelevant to the description are omitted, and the same reference numerals are assigned to the same or similar elements throughout the specification.

In addition, the terms or words used in the present specification and claims should not be construed as being limited to the ordinary or dictionary meanings, and should be understood as having meanings and concepts consistent with the technical spirit of the present invention based on the principle that the inventor can appropriately define the concepts of terms in order to explain the invention in the best way.

Figure 1:
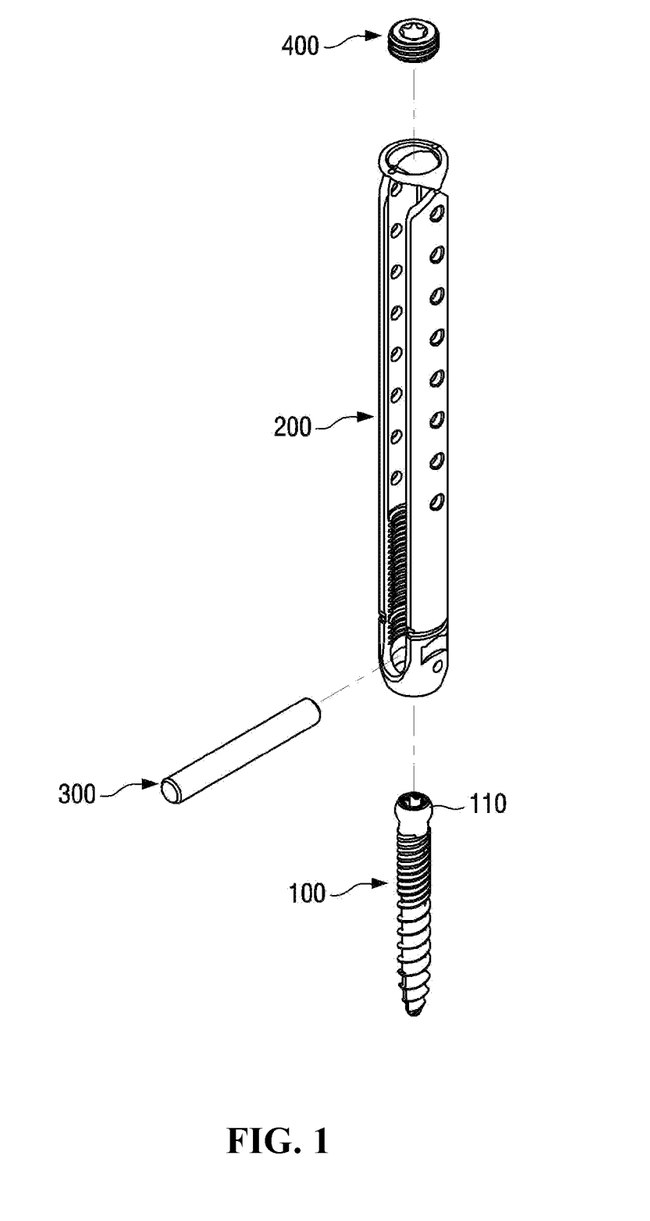
FIG. 1 illustrates an exploded state of each component of a bone fixation screw structure according to an embodiment of the present invention.
Figure 2:
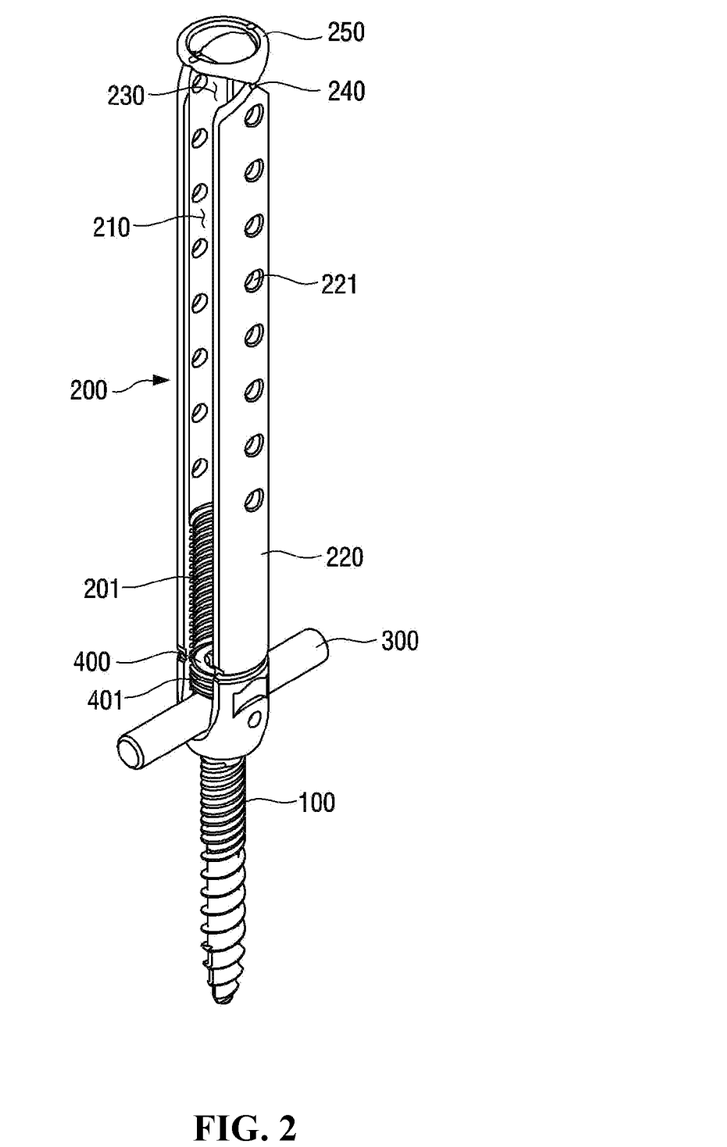
FIG. 2 illustrates the overall appearance of the bone fixation screw structure according to an embodiment of the present invention.

FIG. 1 illustrates an exploded state of each component of a bone fixation screw structure according to an embodiment of the present invention, and FIG. 2 illustrates the overall appearance of the bone fixation screw structure according to an embodiment of the present invention.

As illustrated therein, the bone fixation screw structure according to the present invention includes a bone screw 100, a receiver 200, a rod 300, and a fastening screw 400, in order to physically correct or fix the vertebrae in a state of being joined to each of adjacent vertebrae.

The bone screw 100 has a screw thread formed in the outer surface thereof so that it may be inserted into the bone, and a spherical head 110 having any shape such as a truncated sphere, an oval sphere, or an egg shape is formed at the upper end thereof. A groove for a tool is formed in the spherical head 110 so that a working tool is fitted thereto to rotate the bone screw 100.

The receiver 200 provides a space that is able to accommodate the bone screw 100, the rod 300, and the fastening screw 400. The lower end of the receiver 200 is open, so the spherical head 110 of the bone screw 100 may be seated therein, and the rod 300 and the fastening screw 400 are inserted into the upper side of the receiver. The receiver 200 preferably has a length of about 15 to 150 mm.

The rod 300 serves to interconnect and fix bone screws 100 inserted into respective vertebrae. The rod 300 is preferably disposed almost parallel to the longitudinal direction of the spine.

The fastening screw 400 has a male threaded portion 401 formed on the outer surface thereof so as to be engaged with the female threaded portion 201 formed inside the receiver 200, and a groove for a tool is formed in the upper end thereof so that a working tool is fitted thereto to rotate the fastening screw 400, like the spherical head 110.

The assembly of the bone fixation screw structure is completed by the user in a manner such that the bone screw 100 is seated at the lower side of the receiver 200, the rod 300 and the fastening screw 400 are inserted into the upper side of the receiver 200, and then these components are joined together.

As illustrated in the drawings, a pair of openings 210 is formed at facing sides of the receiver 200. The pair of openings 210 is disposed to face each other at the sides of the receiver 200, and each takes an open form along the longitudinal direction of the receiver 200. The rod 300, the fastening screw 400, or an insert component connected to the rod may be inserted through the pair of openings 210.

A pair of closures 220 is formed at remaining facing sides of the receiver 200. The pair of closures 220 is disposed to face each other at the sides of the receiver 200, and each takes the form of being closed along the longitudinal direction of the receiver 200.

Specifically, the pair of openings 210 is formed to face each other at the sides of the receiver 200, and the pair of closures 220 is formed to face each other at the remaining sides of the receiver orthogonal to the pair of openings 210.

Figure 3:
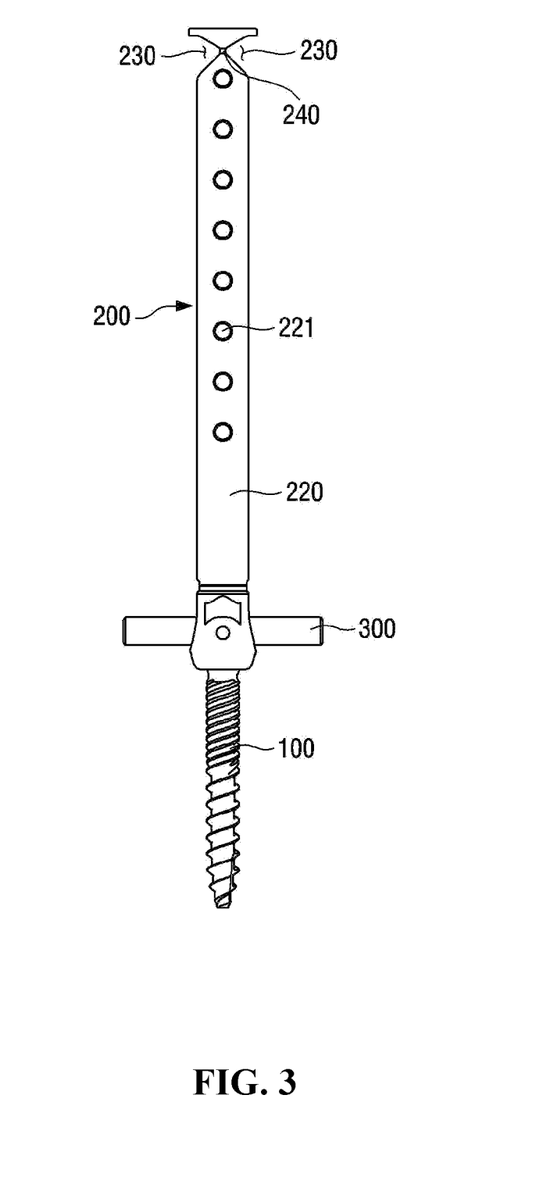
FIG. 3 illustrates the left side of the bone fixation screw structure according to an embodiment of the present invention.
Figure 4:
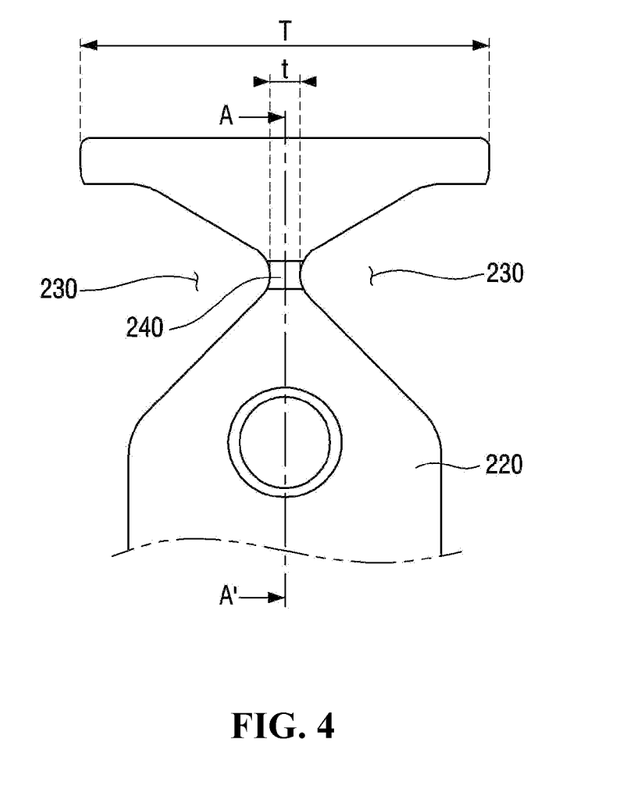
FIG. 4 illustrates the upper portion of a closure according to an embodiment of the present invention.
Figure 5:
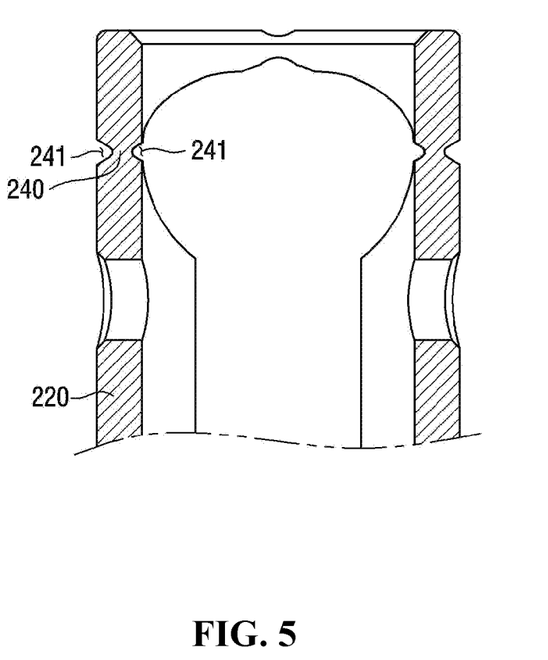
FIG. 5 illustrates a cross-sectional view taken along the line A-A' of FIG. 4.

FIG. 3 illustrates the left side of the bone fixation screw structure according to an embodiment of the present invention, FIG. 4 illustrates the upper portion of the closure according to an embodiment of the present invention, and FIG. 5 illustrates a cross-sectional view taken along the line AA' of FIG. 4.

As illustrates therein, the closure 220 is formed in a closed shape along the longitudinal direction of the receiver 200, and at least one concave portion 230 is formed at the upper end of the closure 220.

Here, a plurality of through-holes 221 is spaced apart from each other in the closure 220 along the longitudinal direction. The plurality of through-holes 221 serves to determine the height at which the bone screw 100 is implanted into the affected part, and provides passages through which pins (not shown) may be inserted in order to temporarily fix some tools in the receiver 200.

The concave portion 230 is provided in a form that is recessed toward a center direction by cutting a portion of the closure 220, and preferably, a pair of concave portions is formed to face each other.

In the illustrated embodiment, the concave portion 230 is formed as a cut slope tapered at a predetermined angle toward the center direction from the outer surface of the closure 220, but is not limited thereto, and may be formed in various shapes, such as a rectangle-shaped cut slope, a circle-shaped cut slope, an oval-shaped cut slope, etc.

A pair of concave portions 230 facing each other is connected to each other via a concave cutout 240. The concave cutout 240 is formed at a position at which the width of the closure 220 is narrowest due to the cut concave portion 230.

As illustrated in FIG. 4, the width t of the concave cutout 240 is preferably formed to be smaller than the outermost diameter T of the receiver 200.

Moreover, it is preferable that at least one concave notch 241 be formed in the outer surface or the inner surface of the concave cutout 240.

The concave notch 241 is recessed inwards from the outer surface of the concave cutout 240, or is recessed outwards from the inner surface of the concave cutout 240.

In the illustrated embodiment, a pair of concave notches 241 is formed to face each other in the inner and outer surfaces of the concave cutout 240, but the present invention is not limited thereto, and the concave notch may be formed only on one side.

As described above, in the present invention, the structure may be easily changed from a closed type to an open type by cutting the concave cutout 240 that connects the concave portions 230 to each other. When the concave cutout 240 is cut using a tool, the remainder thereof is not left behind in the vicinity thereof, so the possibility of interference with the rod 300 or the insert component may be fundamentally prevented.

Figure 6:
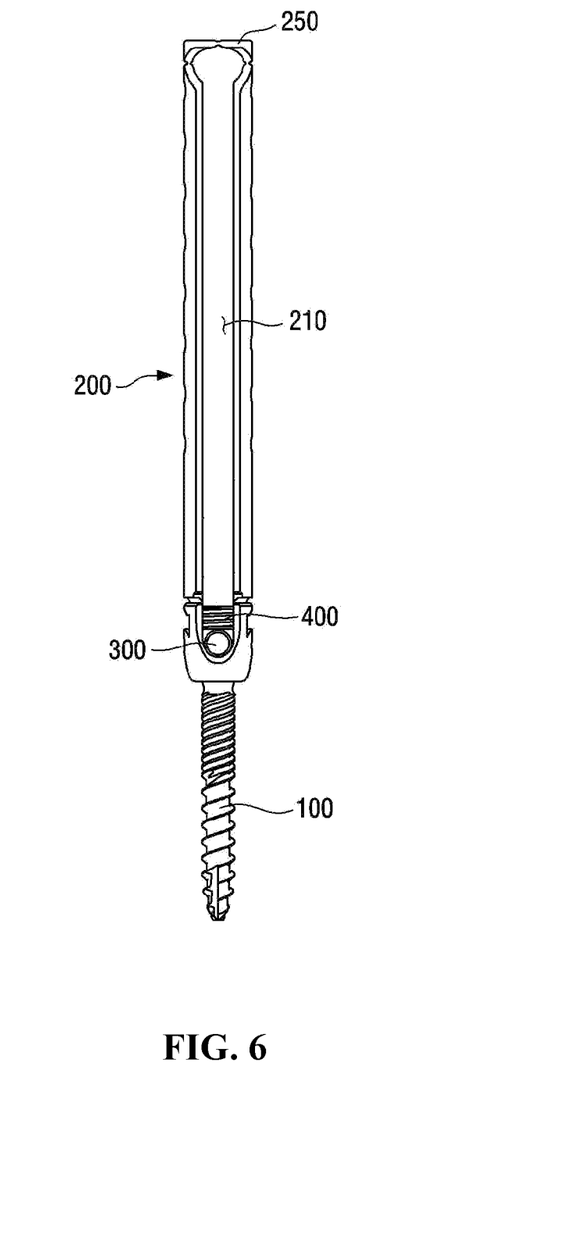
FIG. 6 illustrates the front of the bone fixation screw structure according to an embodiment of the present invention.
Figure 7:
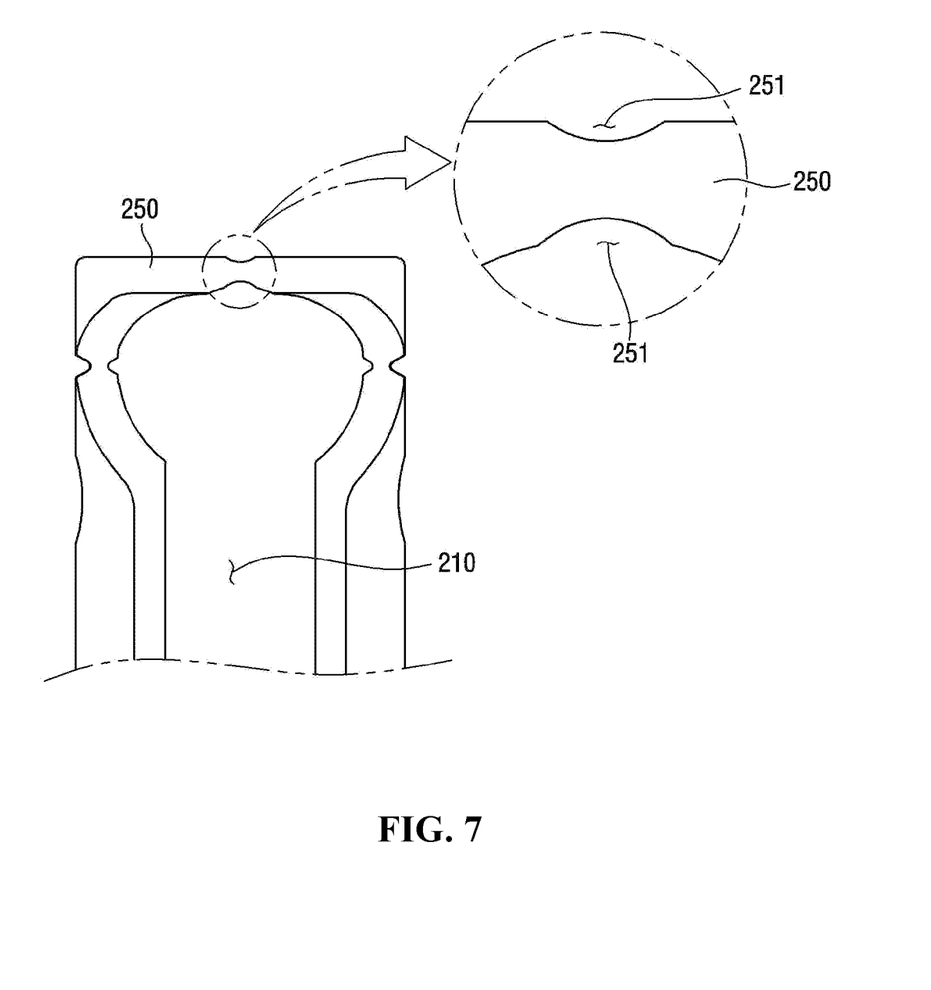
FIG. 7 illustrates the upper portion of an opening according to an embodiment of the present invention.
Figure 8:
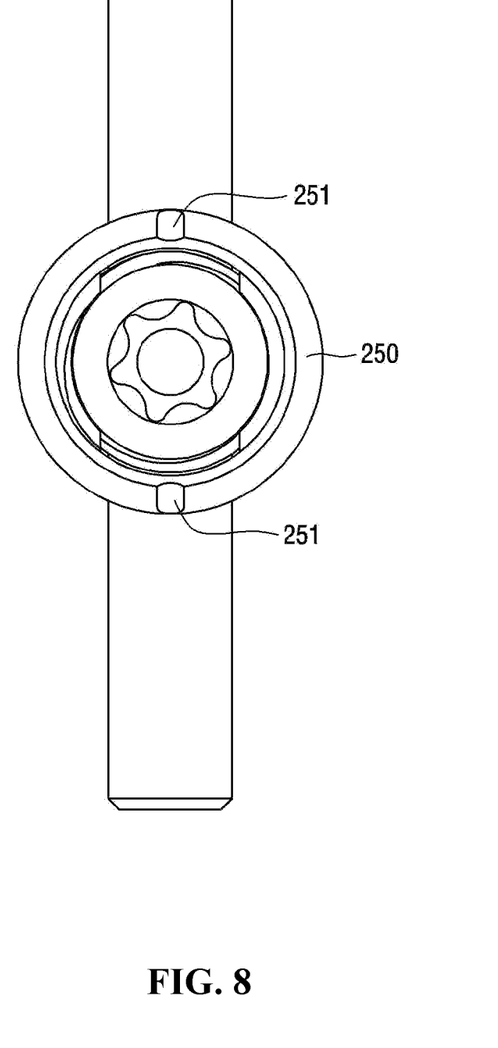
FIG. 8 illustrates a top plan view of the bone fixation screw structure according to an embodiment of the present invention.

FIG. 6 illustrates the front of the bone fixation screw structure according to an embodiment of the present invention, FIG. 7 illustrates the upper portion of the opening according to an embodiment of the present invention, and FIG. 8 illustrates a top plan view of the bone fixation screw structure according to an embodiment of the present invention.

As illustrated therein, the upper ends of the openings 210 are connected to each other by at least one connector 250. In the illustrated embodiment, the connector 250 connects the upper ends of the openings 210 in the form of a circular ring, but the present invention is not limited thereto, and the upper ends thereof may be connected in various forms, such as a polygonal ring, an oval ring, or a blocked surface.

As such, at least one connection notch 251 is formed in the upper surface or the lower surface of the connector 250. The connection notch 251 is recessed downwards from the upper surface of the connector 250, or is recessed upwards from the lower surface of the connector 250.

In the illustrated embodiment, two connection notches 251 are formed in the upper surface of the connector 250 and two connection notches 251 are formed in the lower surface of the connector 250, and these connection notches are disposed to face each other, but the present invention is not limited thereto.

As described above, in the present invention, a closed-type receiver may be changed to an open-type receiver by cutting the concave cutout 240 using a tool, or the pair of closures 220 may be separated from each other by cutting the connection notches 251.

Figure 9:
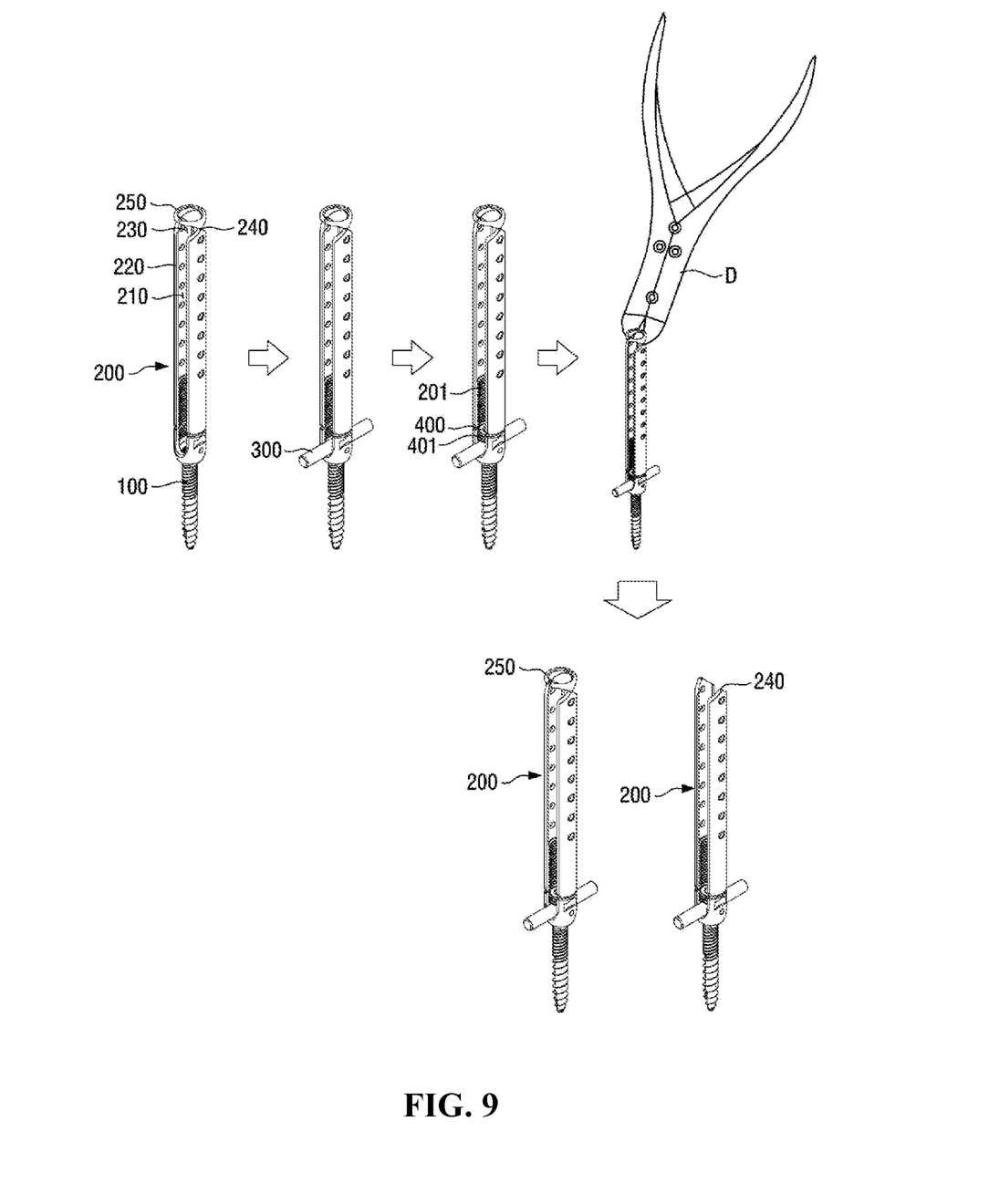
FIG. 9 illustrates a process of assembly of the bone fixation screw structure according to an embodiment of the present invention.

FIG. 9 illustrates the process of assembly of the bone fixation screw structure according to an embodiment of the present invention.

As illustrated therein, the spherical head 110 of the bone screw 100 is inserted into the lower side of the receiver 200 by the user, the rod 300 is inserted into the upper side of the receiver 200, and these components are firmly fixed using the fastening screw 400.

Here, a pair of openings 210 is formed at facing sides of the receiver 200 so that the rod 300 and the fastening screw 400 may be easily inserted into the receiver 200. A male threaded portion 401 is formed on the outer surface of the fastening screw 400 and is engaged with the female threaded portion 201 inside the receiver 200.

Since the upper end of the receiver 200 is closed by at least one connector 250, the assembled bone fixation screw structure functions as a closed type to compensate for distortion during surgery.

On the other hand, when the user prefers an open type, the user cuts the upper end of the receiver 200 using a cutting tool D or the like as illustrated in the drawing, so the receiver 200 is transformed into an open type in which the upper end thereof is open.

As such, one or more concave portions 230 are formed at the upper end of the closure 220, and the concave portions 230 are connected to each other via a concave cutout 240, so the concave cutout 240 may be easily cut by the user, whereby the closed type may be converted into an open type.

In addition, when only the concave cutout 240 is cut, the remainder thereof is not left behind in the vicinity thereof, so the possibility of interference with another rod 300 or an insert component joined to the rod may be completely prevented.

Furthermore, the connection notches 251 formed in the connector 250 that interconnects the upper ends of the openings 210 are cut with the cutting tool D by the user, whereby the pair of closures 220 may be separated from each other.

As is apparent from the above description, the present invention effectively makes it easy for a user to change the closed-type receiver into the open-type receiver by cutting the concave cutout that interconnects one or more concave portions formed at the end of the closure.

In addition, the present invention has the advantage of being able to fundamentally prevent the possibility of interference with a rod or an insert component because the remainder of the concave cutout is not left behind in the vicinity thereof when the concave cutout is cut using a tool.

Moreover, since the present invention can be easily applied to a closed-type receiver or an open-type receiver according to the type desired by the user, products can be manufactured by unifying product types, thereby improving production efficiency.

Although the embodiments of the present invention and the appended drawings have been disclosed for illustrative purposes, those skilled in the art will appreciate that various modifications, additions and substitutions are possible, without departing from the scope and spirit of the invention as disclosed in the accompanying claims.

The invention claimed is:

1. A bone fixation screw structure comprising:
    a receiver configured to provide a space in which a bone screw is seated at a lower end thereof;
    a plurality of pairs of openings formed at facing sides of the receiver and provided in an open form along a longitudinal direction of the receiver; and
    a pair of closures formed at remaining facing sides of the receiver and provided in a closed form along the longitudinal direction of the receiver,
    wherein a pair of concave portions is formed to face each other in each of the pair of closures,
    wherein the pair of concave portions is provided in a form that is recessed toward a center direction,
    wherein the pair of concave portions facing each other is connected to each other via a concave connector,
    wherein the concave connector is formed at a position at which a width of the pair of closures is narrowest and connects each bottom of the pair of concave portions, wherein the pair of concave portions is disposed symmetrically with respect to the concave connector interposed therebetween, and wherein the concave connector is configured to be cut, such that, when the concave connector is cut, the bone fixation screw structure is converted from a closed type into an open type.

2. The bone fixation screw structure of claim 1, wherein a width of the concave connector is smaller than an outermost diameter of the receiver.

3. The bone fixation screw structure of claim 1, wherein at least one concave notch is formed in an outer surface or an inner surface of the concave connector, and wherein the at least one concave slot is recessed inwards from the outer surface of the concave connector, or is recessed outwards from the inner surface of the concave connector.

4. The bone fixation screw structure of claim 1, wherein ends of the pair of openings are connected to each other by at least one connector.

5. The bone fixation screw structure of claim 4, wherein at least one connection notch is formed in an upper surface or a lower surface of the at least one connector.

6. The bone fixation screw structure of claim 1, wherein the plurality pairs of openings include a plurality of through-holes spaced apart from each other in the longitudinal direction of the receiver on each of the pair of closures.

* * * * *